(12) United States Patent
Hsu et al.

(10) Patent No.: US 11,602,593 B2
(45) Date of Patent: Mar. 14, 2023

(54) INFUSION PUMP WITH ELONGATION SENSOR

(71) Applicant: Avent, Inc., Alpharetta, GA (US)

(72) Inventors: Kenneth C. Hsu, Tustin, CA (US); Steve S. Khalaj, Laguna Hills, CA (US); Paul D. Jun, La Crescenta, CA (US); John A. Rotella, San Diego, CA (US); James Lee Shippy, III, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 86 days.

(21) Appl. No.: 15/781,181

(22) PCT Filed: Dec. 15, 2016

(86) PCT No.: PCT/US2016/066764
§ 371 (c)(1),
(2) Date: Jun. 4, 2018

(87) PCT Pub. No.: WO2017/106408
PCT Pub. Date: Jun. 22, 2017

(65) Prior Publication Data
US 2019/0001054 A1 Jan. 3, 2019

Related U.S. Application Data

(60) Provisional application No. 62/268,612, filed on Dec. 17, 2015.

(51) Int. Cl.
*A61M 5/142* (2006.01)
*A61M 5/152* (2006.01)
(Continued)

(52) U.S. Cl.
CPC .............. *A61M 5/152* (2013.01); *A61J 1/05* (2013.01); *A61M 5/16813* (2013.01);
(Continued)

(58) Field of Classification Search
CPC .............. A61M 5/14593; A61M 5/152; A61M 5/15486; A61M 5/148; A61M 5/1483;
(Continued)

(56) References Cited

U.S. PATENT DOCUMENTS 3,993,069 A 11/1976 Buckes et al.
5,080,652 A 1/1992 Sancoff et al.
(Continued)

FOREIGN PATENT DOCUMENTS

CN 1997411 A 7/2007
DE 10 2013 111 800 A1 4/2015
(Continued)

OTHER PUBLICATIONS

International Search Report and Written Opinion for PCT/US2016/066764, dated Apr. 4, 2017, 15 pages.
(Continued)

*Primary Examiner* — Nathan R Price
*Assistant Examiner* — Tania Ismail
(74) *Attorney, Agent, or Firm* — Meunier Carlin & Curfman LLC

(57) ABSTRACT

An elastomeric pump having at least one sensor for sensing changes in elongation of a bladder of the pump is provided. Also provided is an infusion assembly including an elastomeric pump having a bladder, at least one sensor for sensing changes in elongation of the bladder, and an indicator for providing one or more outputs of the sensor. The sensor may be a flexible sensor positioned in contact with the bladder of the pump, or a dielectric material may be incorporated into the material the bladder is made from such that the dielectric elastomer material of the bladder forms the sensor.

17 Claims, 10 Drawing Sheets

(51) Int. Cl.
    *A61M 5/168* (2006.01)
    *A61J 1/05* (2006.01)
    *A61M 5/145* (2006.01)
    *A61M 5/148* (2006.01)
    *G01B 7/16* (2006.01)

(52) U.S. Cl.
    CPC ......... *A61M 5/16854* (2013.01); *A61M 5/145* (2013.01); *A61M 5/148* (2013.01); *A61M 5/1483* (2013.01); *A61M 5/1486* (2013.01); *A61M 5/14593* (2013.01); *A61M 2205/3317* (2013.01); *A61M 2205/3553* (2013.01); *G01B 7/16* (2013.01); *G01B 7/22* (2013.01)

(58) Field of Classification Search
    CPC ................ A61M 5/1486; A61M 5/145; A61M 5/16854; A61M 5/16813; A61M 2025/3337; A61M 2025/3382; A61M 2025/3317; A61M 2025/3584; A61M 2025/502; A61M 2025/587; G01B 7/16; G01B 7/22
    See application file for complete search history.

(56) References Cited

U.S. PATENT DOCUMENTS

| | | | |
|---|---|---|---|
| 5,105,983 | A | 4/1992 | Sancoff et al. |
| 5,209,654 | A * | 5/1993 | Lofsjogard Nilsson ..................... A61M 60/40 417/478 |
| 5,284,481 | A | 2/1994 | Soika et al. |
| 6,350,253 | B1 | 2/2002 | Deniega et al. |
| 6,981,967 | B2 * | 1/2006 | Massengale ........ A61M 5/1424 604/174 |
| 7,959,623 | B2 | 6/2011 | Massengale |
| 2002/0183693 | A1 | 12/2002 | Peterson et al. |
| 2003/0040722 | A1 | 2/2003 | Massengale et al. |
| 2005/0267413 | A1 * | 12/2005 | Wang ................ A61M 5/16886 604/131 |
| 2013/0123694 | A1 * | 5/2013 | Subramaniyan ..... A61B 5/6853 604/100.01 |
| 2013/0274712 | A1 * | 10/2013 | Schecter ............... A61M 25/10 604/510 |
| 2014/0228758 | A1 * | 8/2014 | Chi ...................... A61M 5/148 604/132 |
| 2015/0123647 | A1 | 5/2015 | Gisby et al. |

FOREIGN PATENT DOCUMENTS

| | | | | |
|---|---|---|---|---|
| DE | 102013111800 A1 * | 4/2015 | ........ | A61M 5/16809 |
| JP | 2010043881 A | 2/2010 | | |
| JP | 2013072063 A | 4/2013 | | |
| JP | 2009020006 A | 6/2013 | | |
| JP | 2013521993 T | 6/2013 | | |
| WO | WO 02/098493 A1 | 12/2002 | | |
| WO | 2011119810 A | 9/2011 | | |
| WO | WO 2012/178004 A2 | 12/2012 | | |
| WO | WO 2014/123431 A2 | 8/2014 | | |
| WO | WO-2014144557 A2 * | 9/2014 | ........ | A61M 5/16886 |
| WO | WO 2015/053638 A1 | 4/2015 | | |

OTHER PUBLICATIONS

English Translation of Second Office Action issued in CN Application No. 201680074476.7; dated Dec. 1, 2020; 21 pages.
Notice of Acceptance dated Mar. 22, 2021, in AU application No. 2016370676, 3 pages.
English Translation of Office Action issued in JP Application No. 2018-530840; dated Dec. 1, 2020; 6 pages.
Translation of Office Action issued in JP Application No. 2018-530840; dated Mar. 16, 2021; 8 pages.

* cited by examiner

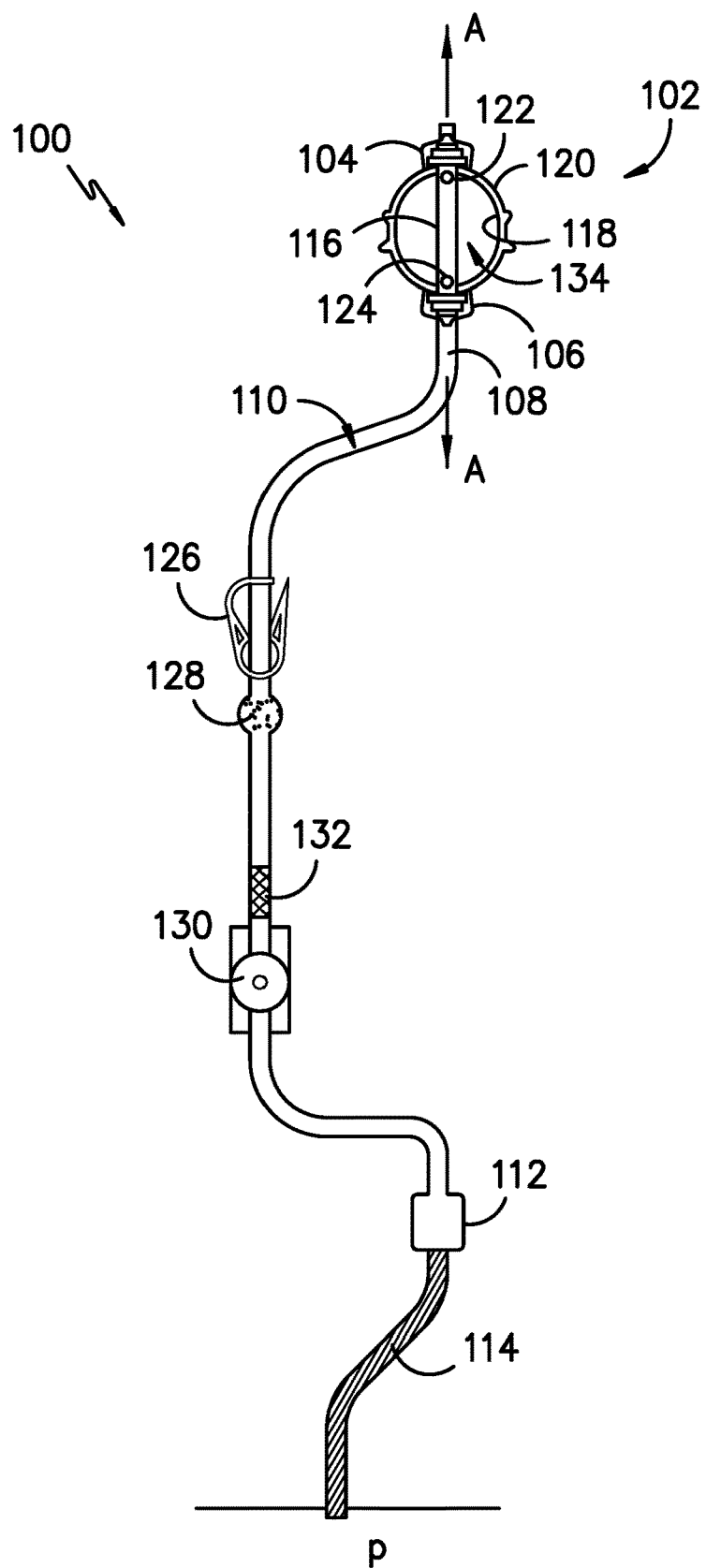
FIG. -1-

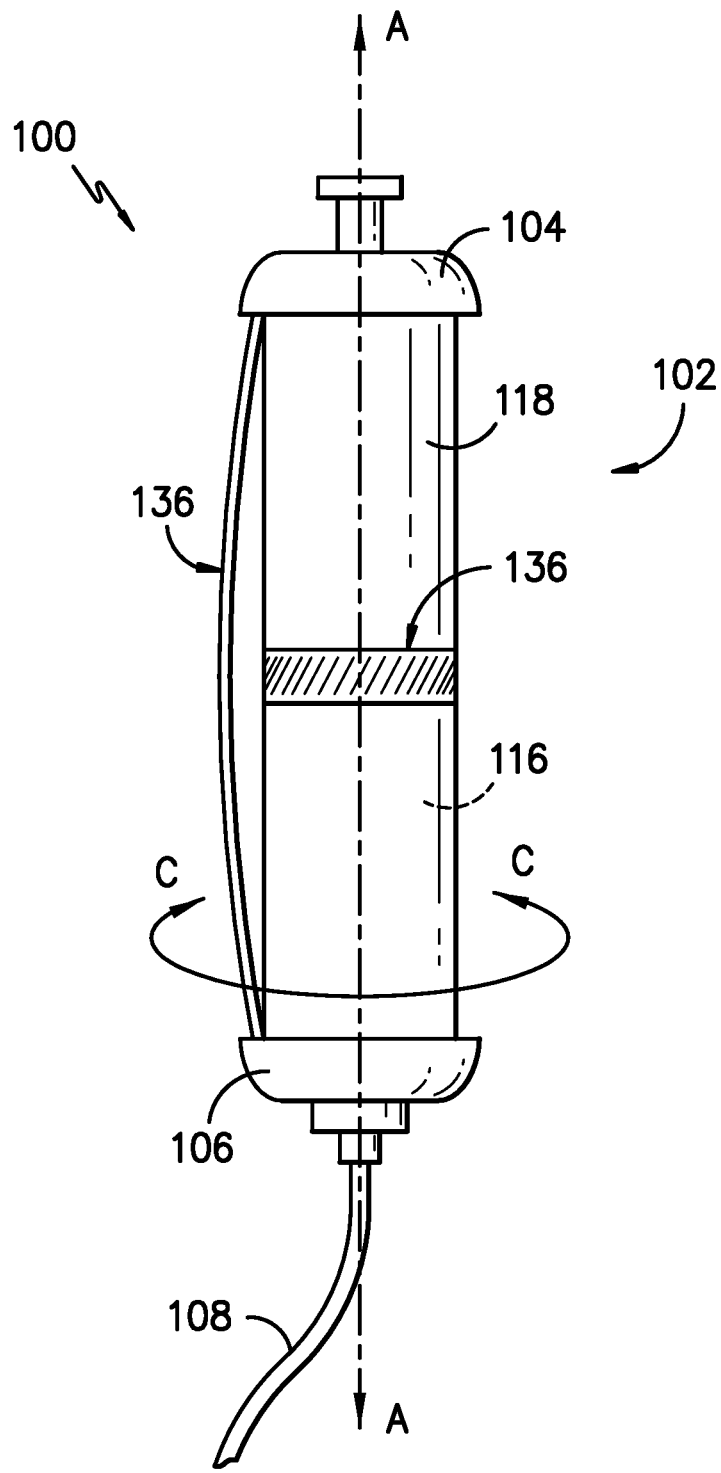
FIG. -2-

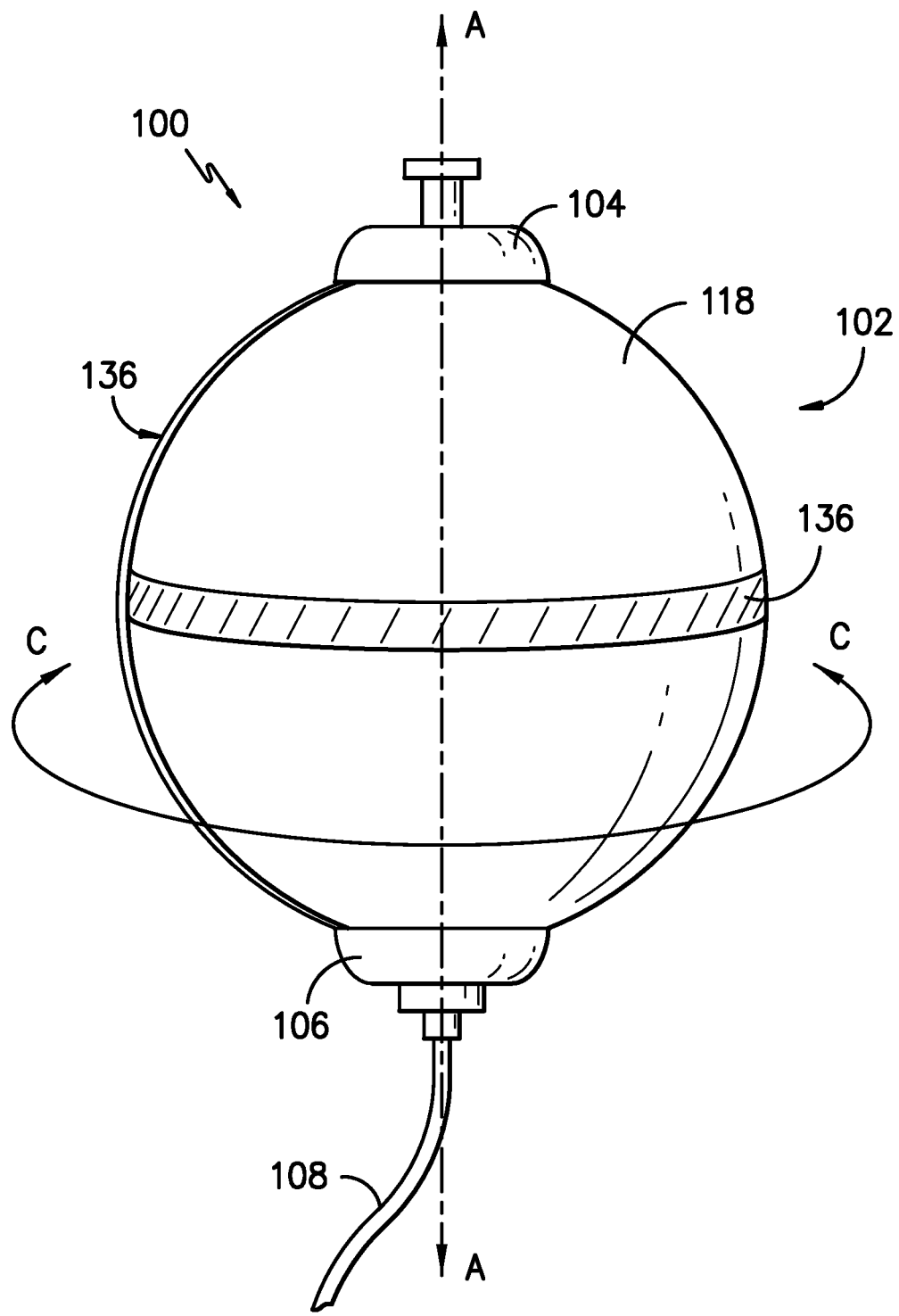
FIG. -3-

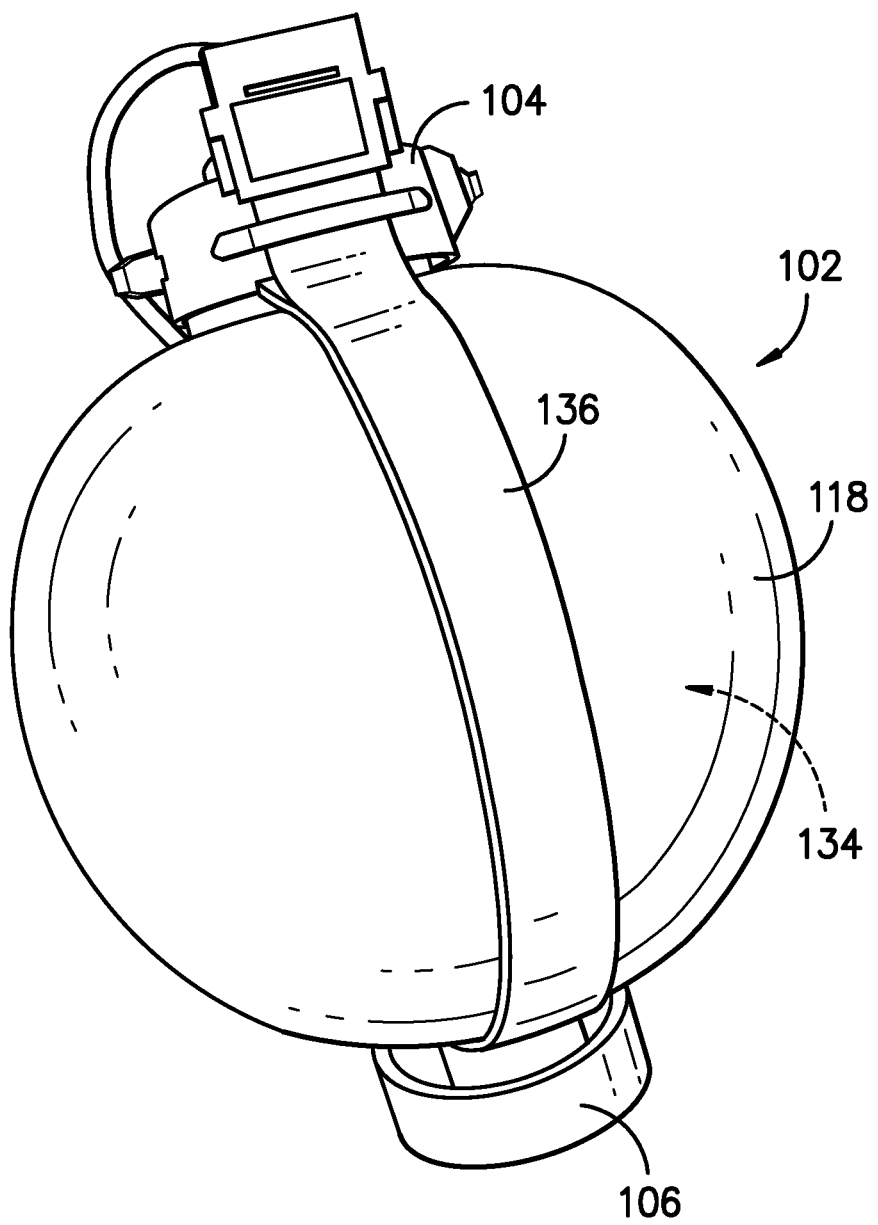
FIG. -4-

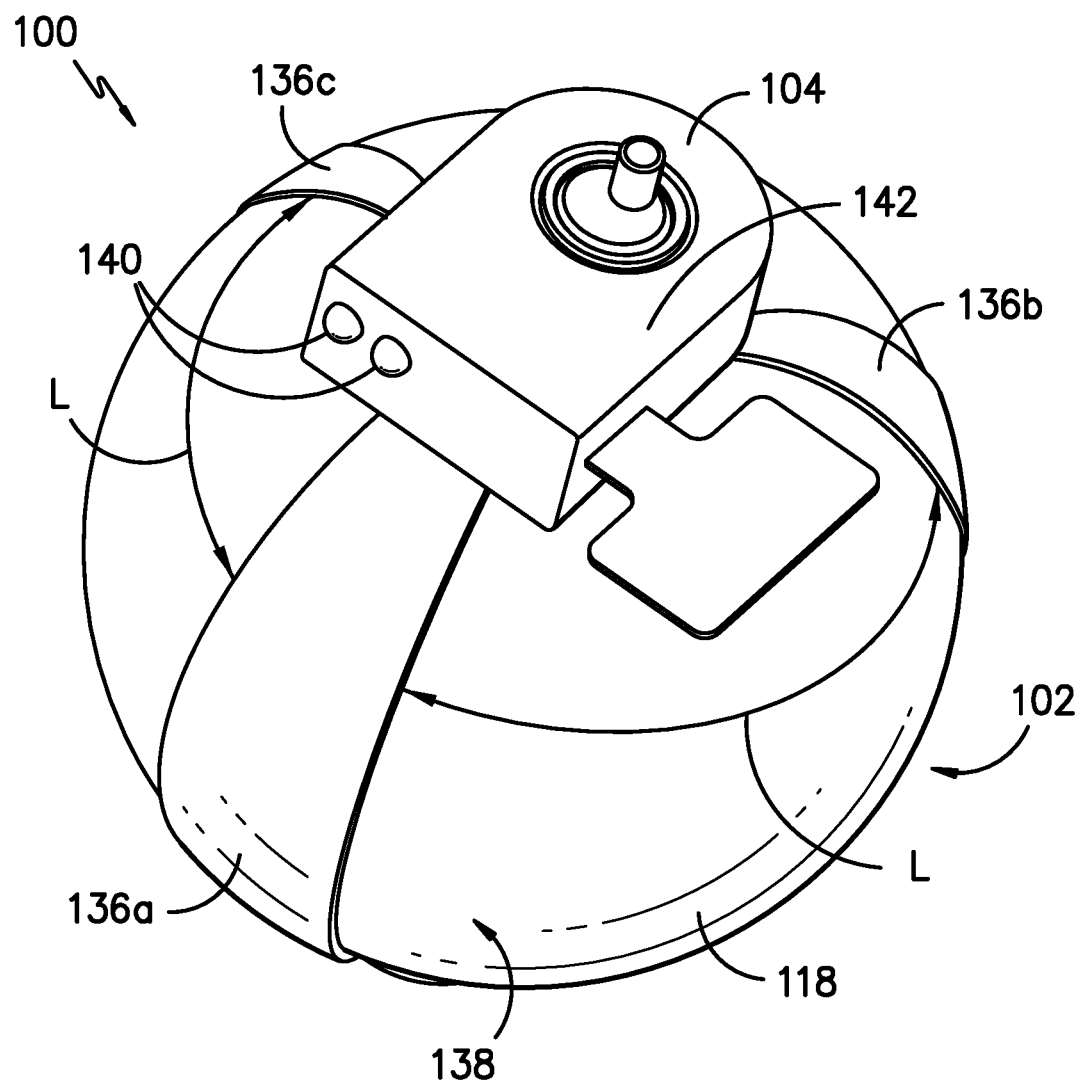
FIG. -5-

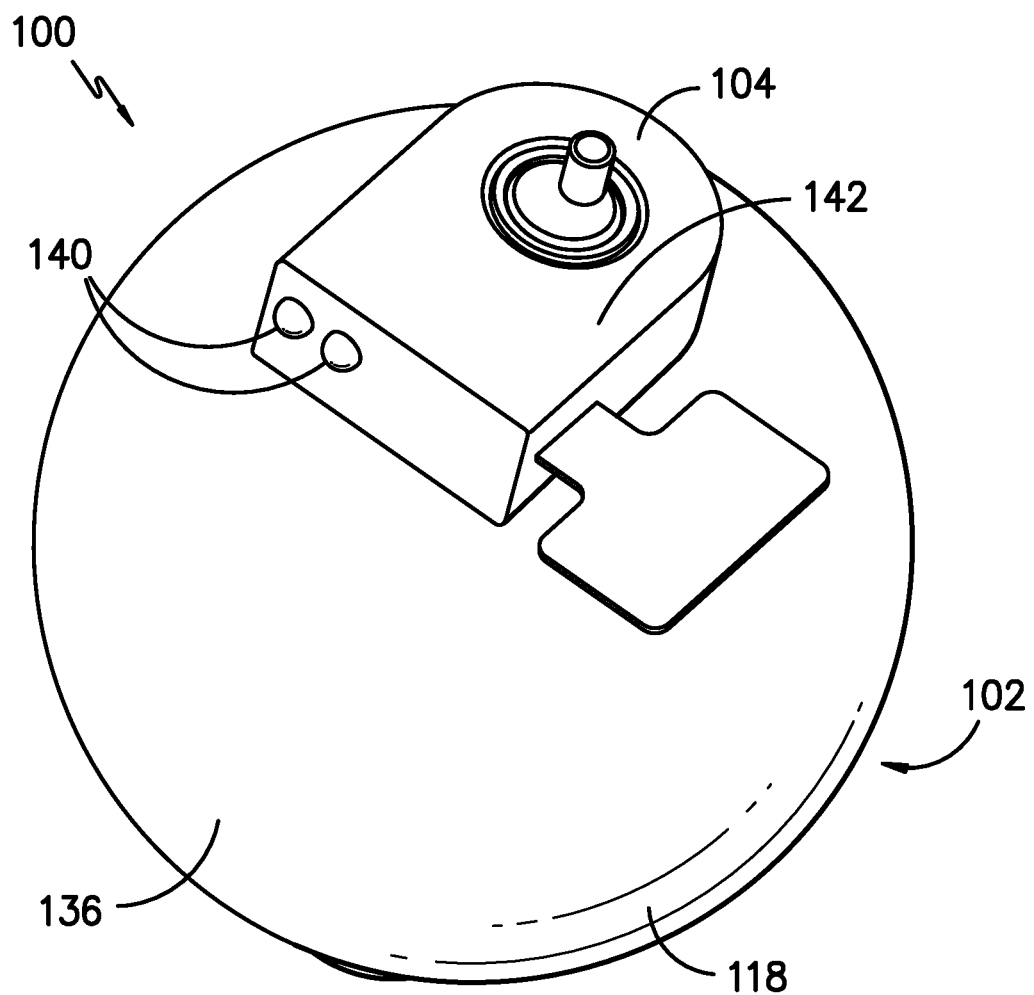
FIG. -6-

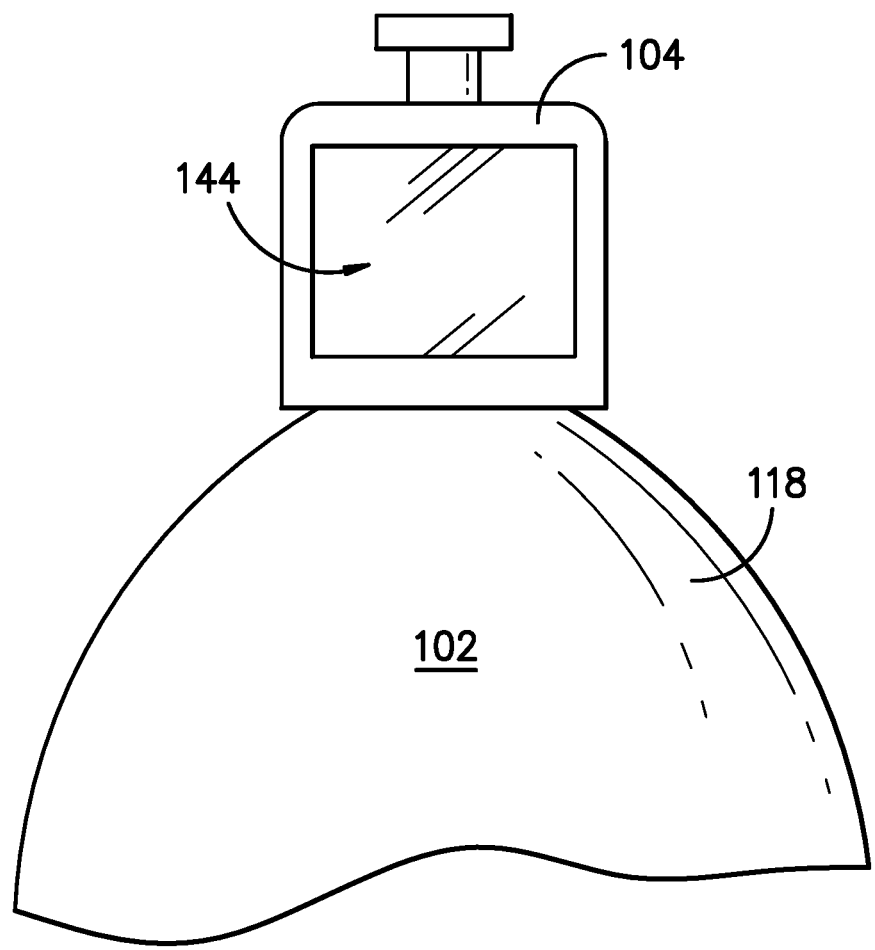
FIG. -7-

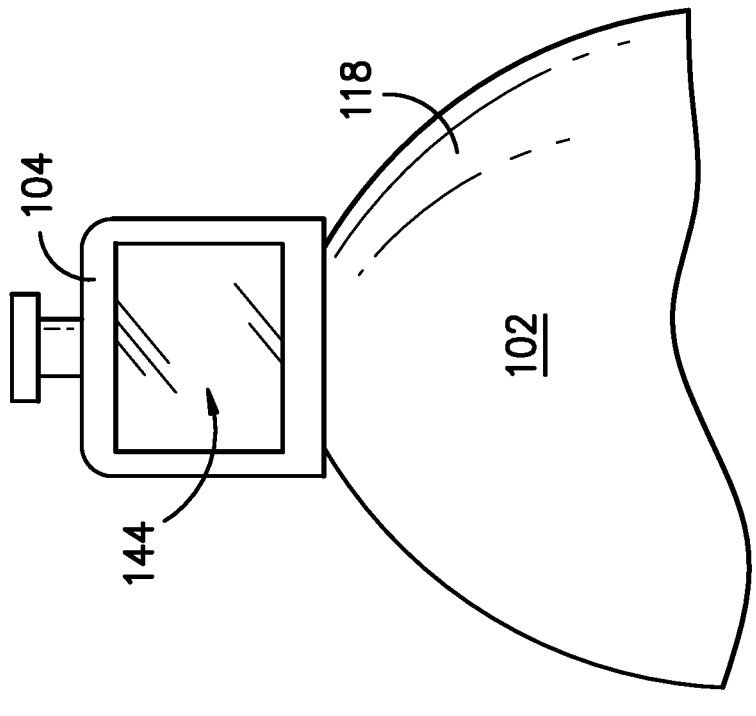
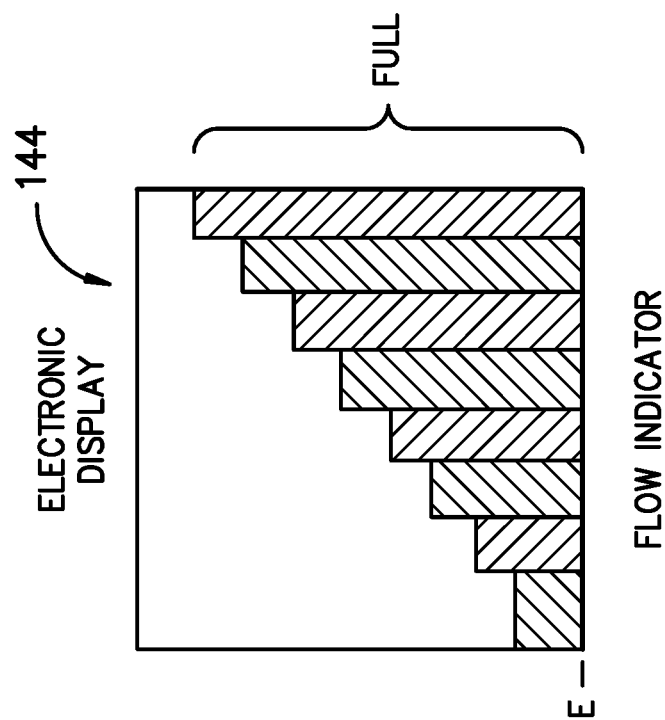
FIG. -8-

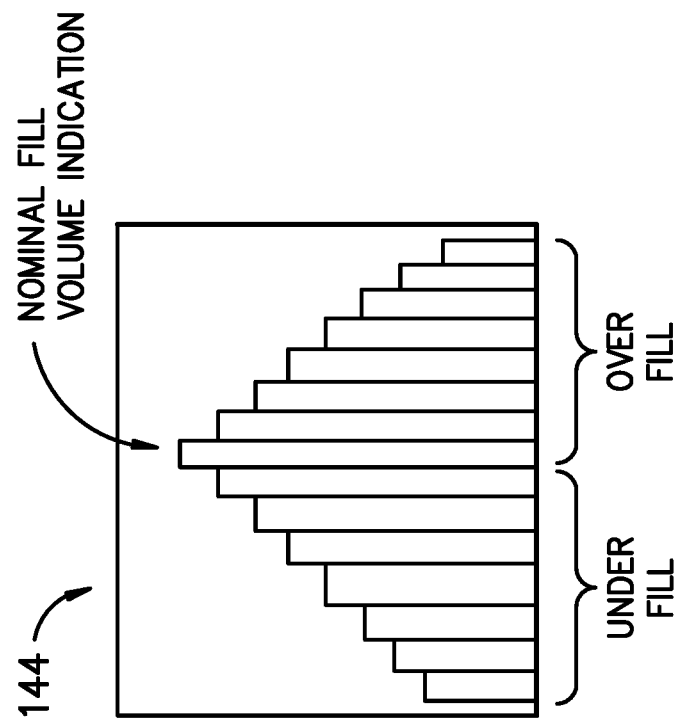
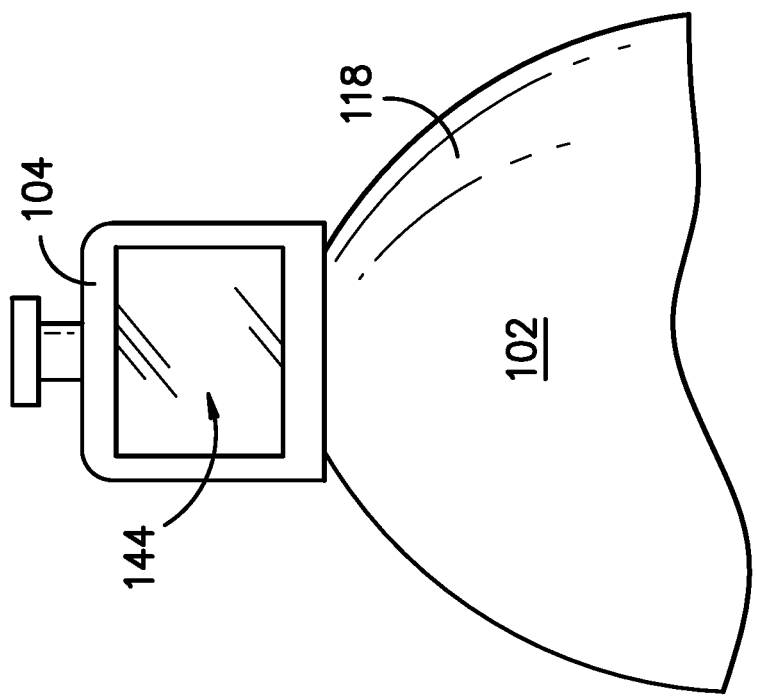
FIG. -9-

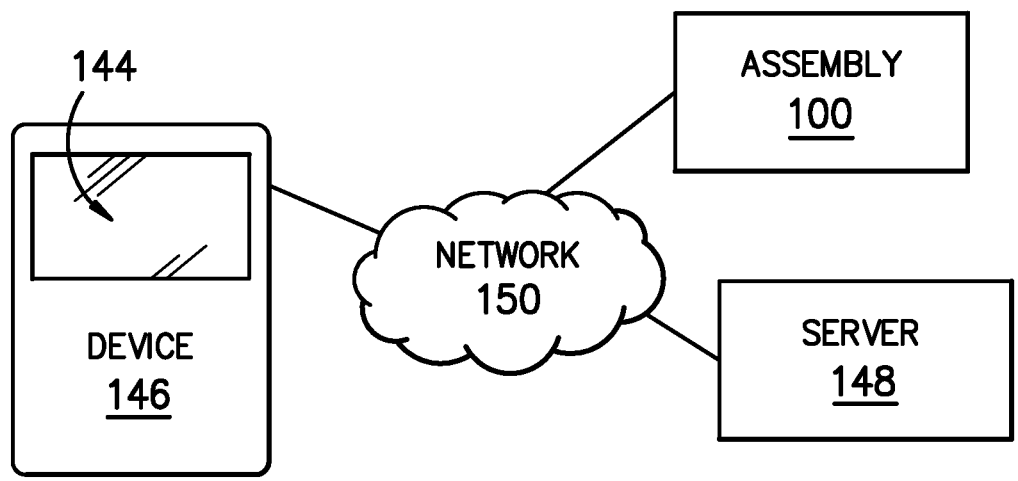
FIG. -10-
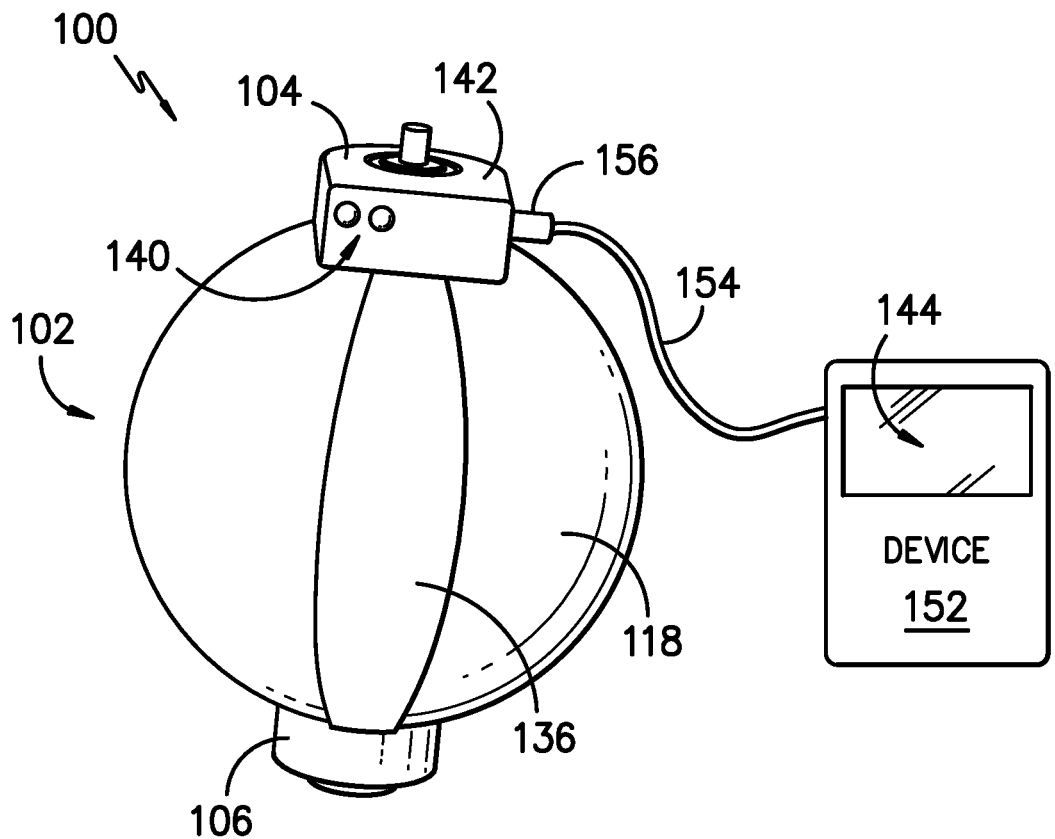
FIG. -11-

INFUSION PUMP WITH ELONGATION SENSOR

RELATED APPLICATION

The present application is the national stage entry of International Patent Application No. PCT/US2016/066764 having a filing date of Dec. 15, 2016, which claims priority to U.S. provisional application Ser. No. 62/268,612, filed on Dec. 17, 2015, both of which are incorporated herein in their entirety by reference thereto.

FIELD OF THE INVENTION

The present invention relates to liquid dispensing apparatus and, more particularly, to an infusion apparatus or assembly for delivering intravenous drugs to a patient having a sensor for sensing the elongation of a bladder for dispensing the intravenous drugs and translating the elongation to a pressure and/or flow change.

BACKGROUND

It is often necessary to intravenously supply patients with pharmaceutically active liquids at a controlled rate over a period of time. Desirably, a patient remains in an ambulatory state while receiving the intravenous supply of pharmaceutically active liquids. Prior art devices for accomplishing this purpose typically include an inflatable elastomeric bladder forming a liquid container and have a device, such as a flow control valve, and tubing for supplying the liquid to the patient. The bladder has walls that are forced to expand when filled with the liquid and provide the pressure for expelling the liquid.

One drawback of conventional devices is that it is difficult for users, such as the patient or a caregiver, to discern whether the pump is providing the liquid, i.e., whether the device is dispensing liquid from the bladder. Accordingly, a device having an elastomeric pump and including features for sensing a change in elongation of the bladder and communicating information about the operation of the pump based on the change in elongation would be beneficial.

SUMMARY

The present invention provides an elastomeric pump having at least one sensor for sensing changes in elongation of a bladder of the pump. The present invention also provides an infusion assembly including an elastomeric pump having a bladder, at least one sensor for sensing changes in elongation of the bladder, and an indicator for providing one or more outputs of the sensor. The sensor may be a flexible sensor positioned in contact with the bladder of the pump, or a dielectric material may be incorporated into the material the bladder is made from such that the dielectric elastomer material of the bladder forms the sensor.

Additional aspects and advantages of the invention will be set forth in part in the following description, may be apparent from the description, or may be learned through practice of the invention.

In one aspect, the present subject matter is directed to an elastomeric pump for an infusion assembly. The pump includes an upper support member and a lower support member spaced apart from the upper support member along an axial direction. The pump further includes an expandable bladder defining a chamber. The bladder extends from the upper support member to the lower support member. The pump also has at least one flexible sensor extending between the upper support member and the lower support member, and the sensor is in contact with the bladder to measure a change in elongation of the bladder.

It should be appreciated that the pump may be further configured with any of the additional features as described herein. For example, in some embodiments, the sensor is a dielectric elastomer sensor. In an exemplary embodiment, the pump comprises three sensors that extend between the upper support member and the lower support member. The three sensors may be evenly spaced such that a same circumferential length separates each sensor at an axial position along the bladder. In some embodiments, the one or more sensors extend generally axially from the upper support member to the lower support member. In other embodiments, the one or more sensors extend generally radially, or orthogonal to the axial direction.

In some embodiments, the pump includes an outer layer positioned radially outward of the bladder. In such embodiments, the bladder is an inner layer, and the at least one sensor may be positioned between the outer layer and the bladder.

In still other embodiments, the at least one sensor can measure a change in elongation of the bladder of up to about 300%. Further, the pump may also include at least one indicator for providing information about the pump. The information may be based on the change in elongation of the bladder. In one embodiment, the at least one indicator comprises a light emitting diode. In another embodiment, the at least one indicator comprises a display incorporated into the infusion assembly. As such, in alternative embodiments the display may be positioned at the upper support member, attached to the upper support member, or incorporated into the upper support member. In still other embodiments, the display may be incorporated into a wireless user device or into a wired user device that is selectively plugged into a control housing of the pump.

In another aspect, the present subject matter is directed to an elastomeric pump for an infusion assembly. The pump includes an upper support member and a lower support member spaced apart from the upper support member along an axial direction. The pump also includes an expandable bladder defining a chamber. The bladder extends from the upper support member to the lower support member and is made from a material comprising an elastomer and a dielectric. The dielectric in the bladder material forms a sensor for measuring a change in elongation of the bladder.

It should be understood that the pump may be further configured with any of the additional features as described herein. As an example, in some embodiments, the pump further comprises an outer layer positioned radially outward of the bladder such that the bladder is an inner layer. In other embodiments, the at least one sensor can measure a change in elongation of the bladder of up to about 300%. Further, the pump may also include at least one indicator for providing information about the pump. The information may be based on the change in elongation of the bladder. In one embodiment, the at least one indicator comprises a light emitting diode. In another embodiment, the at least one indicator comprises a display incorporated into the infusion assembly. As such, in alternative embodiments the display may be positioned at the upper support member, attached to the upper support member, or incorporated into the upper support member. In still other embodiments, the display may be incorporated into a wireless user device or into a wired user device that is selectively plugged into a control housing of the pump.

In still another aspect, the present subject matter is directed to an infusion assembly. The infusion assembly includes an elastomeric pump having an expandable bladder defining a chamber; at least one flexible sensor in contact with the bladder; and at least one indicator for indicating one or more outputs of the sensor. It should be appreciated that the infusion assembly may be further configured with any of the additional features as described herein. As an example, in some embodiments, the at least one sensor is a dielectric elastomer sensor.

In other embodiments, the infusion assembly further comprises at least three sensors. The at least three sensors extend between an upper support member and a lower support member of the pump. In some embodiments, the at least three sensors are evenly spaced such that a same circumferential length separates each sensor at an axial position along the bladder. In other embodiments, the one or more sensors extend generally axially from the upper support member to the lower support member. In some embodiments, the one or more sensors extend generally radially, or orthogonal to the axial direction.

In another embodiment, the pump also includes an outer layer positioned radially outward of the bladder such that the bladder is an inner layer. In such an embodiment, the at least one sensor may be positioned between the outer layer and the bladder.

In some embodiments, the at least one sensor can measure a change in elongation of the bladder of up to about 300%. Further, the at least one indicator may be a light emitting diode. Alternatively or additionally, the at least one indicator may include a display. The pump may include an upper support member spaced apart from a lower support member along an axial direction, and in various embodiments, the display may be positioned at, attached to, or incorporated into the upper support member of the pump. In other embodiments, the display may be incorporated into a wireless user device or into a wired user device that is selectively plugged into a control housing of the pump.

Further, in some embodiments of the infusion assembly, one output of the sensor is a flow rate of fluid from the bladder. Alternatively or additionally, one output of the sensor is a volume of fluid dispensed from the bladder.

In yet another aspect, the present subject matter is directed to an infusion assembly. The infusion assembly includes an elastomeric pump having an expandable bladder. The bladder is made from a material comprising an elastomer and a dielectric. The dielectric in the bladder material forms a sensor for measuring a change in elongation of the bladder. The infusion assembly also includes an indicator for indicating one or more outputs of the sensor.

It should be understood that the infusion assembly may be further configured with any of the additional features as described herein. For example, in some embodiments, the infusion assembly includes an outer layer positioned radially outward of the bladder such that the bladder is an inner layer. In other embodiments, the at least one sensor can measure a change in elongation of the bladder of up to about 300%. Further, the at least one indicator may be a light emitting diode. Alternatively or additionally, the at least one indicator may include a display. The pump may include an upper support member spaced apart from a lower support member along an axial direction, and in various embodiments, the display may be positioned at, attached to, or incorporated into the upper support member of the pump. In other embodiments, the display may be incorporated into a wireless user device or into a wired user device that is selectively plugged into a control housing of the pump.

Moreover, in some embodiments of the infusion assembly, one output of the sensor is a flow rate of fluid from the bladder. Alternatively or additionally, one output of the sensor is a volume of fluid dispensed from the bladder.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a side view of an infusion assembly according to an exemplary embodiment of the present subject matter.

FIG. 2 is a side view of an elastomeric pump in a deflated position, according to an exemplary embodiment of the present subject matter.

FIG. 3 is a side view of the elastomeric pump of FIG. 2 in an inflated position, according to an exemplary embodiment of the present subject matter.

FIG. 4 is a photograph of an elastomeric pump according to an exemplary embodiment of the present subject matter.

FIG. 5 is a top, perspective view of a portion of an infusion assembly according to an exemplary embodiment of the present subject matter.

FIG. 6 is a side, perspective view of a portion of an infusion assembly according to an exemplary embodiment of the present subject matter.

FIG. 7 is a side view of a portion of an elastomeric pump having a display according to an exemplary embodiment of the present subject matter.

FIG. 8 is a side view of a portion of an elastomeric pump and a display of the elastomeric pump according to an exemplary embodiment of the present subject matter.

FIG. 9 is a side view of a portion of an elastomeric pump and a display of the elastomeric pump according to an exemplary embodiment of the present subject matter.

FIG. 10 is a schematic view of a wireless communications system including an infusion assembly and a wireless user device according to an exemplary embodiment of the present subject matter.

FIG. 11 is a side view of a portion of an infusion assembly with a wired user device plugged into or connected to the assembly according to an exemplary embodiment of the present subject matter.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular the naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

FIG. 1 provides a side view of an infusion assembly, e.g., for dispensing a fluid to a patient, according to an exemplary embodiment of the present subject matter. As shown, the exemplary infusion assembly 100 includes an elastomeric pump 102 having an upper support member 104 and a lower support member 106. Infusion assembly 100 defines an axial direction A, and lower support member 106 is spaced apart from upper support member 104 along the axial direction A.

More particularly, pump 102 defines a reservoir that serves as a pressurized fluid source, holding medicinal fluid, such as local anesthetics, and providing a source of fluid under pressure. Pump 102 forces the medicinal fluid through a tubing or conduit 108. Conduit 108 forms a continuous flow path 110 for delivery of the medicinal fluid into a wound site nerve bundle or the blood stream of a patient P. In the depicted exemplary embodiment, conduit or tubing 108 defines an outlet 112 connecting the continuous flow path 110 to a catheter 114 that delivers the medicinal fluid to patient P. In such embodiments, conduit 108 and catheter 114 may together define continuous flow path 110 from pump 102 to patient P.

Further, in some embodiments, infusion assembly 100 may be configured to provide for bolus delivery. In such configurations, conduit 108 may split into a continuous or primary flow path and a controlled bolus flow path (not shown). Thus, medicinal fluid may be delivered into a wound site nerve bundle or the blood stream of patient P from pump 102 via the continuous or primary flow path or from a bolus delivery system via the controlled bolus flow path.

Pump 102 preferably accommodates a volume from about 100 to 500 ml of fluid under a pressure of about 10 to 15 psi. More particularly, pump 102 has an inner core 116 extending between upper support member 104 and lower support member 106 along axial direction A. Inner core 116 is surrounded by an elastomeric bladder 118 within a housing 120. Inner core 114 preferably has an inlet port 122, e.g., to fill bladder 118 with fluid, and an outlet port 124 in fluid communication with conduit 108, e.g., to dispense the fluid from bladder 118 to patient P through flow path 110. Fluid is held under pressure within elastomeric bladder 118 and flows from elastomeric bladder 118 into conduit 108 through outlet port 124, preferably flowing at a controlled and predictable rate. Alternatively, conduit 108 may be sized to serve as a flow restrictor. Further, elastomeric bladder 118 preferably is constructed from a resilient material that may comprise a variety of elastomeric compositions well known in the art, including vulcanized synthetic polyisoprenes, natural latex, natural rubber, synthetic rubber, silicone rubber, or the like.

Exemplary pumps are described in U.S. Pat. Nos. 7,959,623 and 5,254,481, which are hereby incorporated by reference. A variety of other conventional pumps also may be used. For example, the pumps described in U.S. Pat. Nos. 5,080,652 and 5,105,983, which are hereby incorporated by reference, may be used. As will be understood by those of skill in the art, other suitable electronic or mechanical pumps offered by other manufacturers may be used as well.

Continuing with FIG. 1, an optional clamp 126 is positioned in flow path 110 downstream from pump 102. Clamp 126 can compress conduit 108 such that fluid flow from pump 102 through flow path 110 is occluded. Such occlusion is advantageous, e.g., for the transportation and preparation of infusion assembly 100 as described herein. An exemplary clamp 126 is described in U.S. Pat. No. 6,350,253, which is hereby incorporated by reference. However, a variety of other conventional clamps known in the industry may be used to occlude the flow of fluid from pump 102 through flow path 110, such as compression clamps, C clamps, roller clamps, and the like.

An optional filter 128 downstream of clamp 126 separates the fluid from contaminates and other undesired particles that may be found within the fluid. Filter 128 also preferably eliminates air from fluid flow path 110. One such filter 128 is described in U.S. Pat. No. 6,350,253, which is hereby incorporated by reference. Of course, other suitable filters recognized in the industry may be used to capture undesired particles and/or remove air from the system.

As further shown in FIG. 1, an optional flow regulator 130 is positioned in continuous flow path 110. Flow regulator 130 sets the continuous and substantially constant flow rate of fluid from pump 102 to patient P via tubing 108. In some embodiments, the flow rate may be adjusted to a rate within a range, e.g., within a range of about 0.5 to about 14 cubic centimeters of fluid per hour. Flow regulator 130 may be manually adjustable, if desired, and provided with a dial, switch, or lever with an adjustable flow rate control display corresponding to the range of flow rates. For example, the flow rate range may be from about 1 to about 7 or from about 2 to about 14 cubic centimeters of fluid per hour such that the flow rate control display includes a lowermost value of 1 and an uppermost value of 7 or a lowermost value of 2 and an uppermost value of 14. It will be appreciated that the foregoing flow rate values are only exemplary, and in other embodiments, infusion assembly 100 may have other flow rates and the flow rate may be adjustable within another range of flow rates. Alternatively, a constant flow regulator (i.e., a regulator that is not adjustable) can be employed. For example, an optional flow regulating orifice, such as a glass orifice tube 132, may be employed in the primary or continuous flow path 110. Moreover, in embodiments having a bolus flow path, an optional second flow regulating orifice may be employed in the bolus flow path.

The particular arrangement of clamp 126, filter 128, and flow regulator 130 (or glass tube 132) described herein is merely exemplary. These elements, if present, may be arranged in any order, as will be easily understood by those skilled in the art. Desirably, however, glass orifice tube 132 is located downstream of filter 128 when orifice tube 132 and filter 128 are provided in infusion assembly 100.

Referring now to FIGS. 2 and 3, in the depicted embodiment of infusion assembly 100, bladder 118 extends from upper support member 104 to lower support member 106 and defines a circumferential direction C. Bladder 118 is expandable from a generally deflated position, as shown in FIG. 2, to a generally inflated position, as shown in FIG. 3, as fluid is received within a chamber 134 (FIG. 1) defined by bladder 118. That is, bladder 118 expands or elongates from the deflated position to the inflated position as fluid is introduced into chamber 134 through inlet port 122. Further, bladder 118 contracts from the inflated position to the deflated position as fluid is dispensed from chamber 134 through outlet port 124 and into flow path 110 defined by conduit 108. More particularly, bladder 118 in the deflated position has a generally cylindrical shape, a first circumference, and a first volume $V_1$. In the inflated position, bladder 118 has a generally spherical shape, a second circumference, and a second volume $V_2$. Second volume $V_2$ is greater or larger than first volume $V_1$. Of course, bladder 118 may have other shapes as well, but regardless of its shape, bladder 118 has a greater or larger volume in its inflated position than in its deflated position.

As shown in FIGS. 2, 3, and 4, infusion assembly 100 includes at least one flexible, compliant sensor 136 extending generally axially between upper support member 104 and lower support member 106 and in contact with elastomeric bladder 118. Sensor 136 is positioned within infusion assembly 100 to measure a change in elongation in bladder 118 as bladder 118 expands from its deflated position to its inflated position and/or as bladder 118 contracts from its inflated position to its deflated position. Referring now to FIG. 5, in an exemplary embodiment, infusion assembly 100 includes three sensors 136 to help improve the measurement of the change in elongation of bladder 118 as bladder 118 expands and/or contracts to receive and dispense fluid. That is, multiple sensors 136 obtaining differential readings can help improve the accuracy in measuring the change in elongation of bladder 118. Each of the three sensors 136 extends generally axially between upper support member 104 and lower support member 106 and in contact with bladder 118. Preferably, the three sensors 136 are evenly spaced about the circumference of bladder 118. For example, as illustrated in FIG. 5, at any given axial position, a circumferential distance or length L separates each sensor 136. That is, the same circumferential length L separates a first sensor 136a, a second sensor 136b, and a third sensor 136c. Circumferential length L may vary from one axial position to another, e.g., length L generally is longer or greater at approximately an axial midpoint along an outer surface 138 of bladder 118 and shorter or smaller near upper mounting point 104 and lower mounting point 106.

As stated, sensor 136 is a flexible, compliant sensor that flexes and/or stretches to measure changes in elongation of bladder 118. For example, in certain embodiments, sensor 136 maintains contact with outer surface 138 of bladder 118 as bladder 118 expands with an ingress into chamber 134 and as bladder 118 contracts with an egress of fluid from chamber 134. More generally, each sensor 136 expands or elongates as bladder 118 expands and each sensor 136 contracts as bladder 118 contracts to measure changes in elongation of bladder 118. Sensors 136 generally expand and contract axially but also may expand and contract along the circumferential direction C.

In other embodiments, as further depicted in FIGS. 2 and 3, infusion assembly 100 includes at least one flexible, compliant sensor 136 extending generally circumferentially or radially about bladder 118. For example, one or more sensors 136 may encircle bladder 118 such that sensor(s) 136 extend around the circumference of bladder 118 generally orthogonal to the axial direction A. In such embodiments, sensor(s) 136 generally expand and contract circumferentially or radially, but sensor(s) 136 also may expand and contract axially.

In still other embodiments, pump 102 may be a two layer pump. As an example of a two layer pump, housing 120 is an outer layer of pump 102 and bladder 118 is an inner layer of pump 102. As such, the outer layer 120 is positioned radially outward from the inner layer, bladder 118. Both the outer and inner layers may expand and contract as chamber 134 receives and dispenses fluid. In one embodiment, bladder 118 (the inner layer) comprises a latex material and housing 120 (the outer layer) comprises an expandable non-latex material, such that the portion of pump 102 that patient P may come into contact with is not constructed using a latex material. In such two layer configurations, the one or more sensors 136 may be positioned between the inner and outer layers of pump 102 such that sensors 136 do not come into contact with patient P. Of course, sensors 136 also may be placed adjacent an outer surface of housing 120, i.e., adjacent an outer surface of the outer layer rather than adjacent an inner surface of the outer layer and an outer surface of the inner layer. Because the outer layer expands and contracts as the inner layer expands and contracts, sensors 136 positioned adjacent the outer surface of the outer layer can still measure or sense changes in elongation of the inner layer, i.e., bladder 118.

Alternatively, as generally illustrated in FIG. 6, sensor 136 may comprise a dielectric material embedded or incorporated into the elastomer material of bladder 118. That is, dielectric particles may be included in the elastomeric bladder 118, with the dielectric particles forming sensor 136 for sensing or measuring the change in elongation of bladder 118 as bladder 118 expands and contracts.

Preferably, the at least one sensor 136 is a dielectric elastomer sensor, for example, a dielectric elastomer sensor from StretchSense Limited of Auckland, New Zealand. Dielectric elastomer devices are electromechanical transducers are inherently compliant devices and may be actuators, sensors, or generators. A basic dielectric elastomer device is a laminate of layers of film, including an insulating soft polymer membrane sandwiched between compliant electrodes. More specifically, dielectric elastomer sensors are low stiffness, high strain devices with electrical parameters that are intimately coupled to a mechanical state of the sensor. The electrical parameters may include, e.g., capacitance, the resistance of the electrodes, and the conductivity of the dielectric. For example, the membrane of a dielectric elastomer device preferably is volumetrically incompressible, and as a result, it is possible to relate a change in capacitance between the electrodes to changes in the physical geometry of the dielectric elastomer sensor. Dielectric elastomer sensors and/or features thereof are described in more detail, e.g., in U.S. Patent Application Publication No. 2015/0123647 and International Application Publication Nos. WO 2015/053638 and WO 2014/123431.

Thus, in an exemplary embodiment utilizing a dielectric elastomer sensor 136, sensor 136 may sense or measure changes in capacitance between its electrodes as its elongation changes, which correlates to changes in elongation of bladder 118. Further, the changes in capacitance of sensor 136 and/or the measured change in elongation of bladder 118 can be correlated to various conditions or parameters of pump 102. For example, the change in elongation can be correlated to a flow rate of fluid from pump 102 and/or infusion assembly 100, as well as a volume or pressure of fluid within pump 102. As a result, sensor 136 can be used to detect flow, no flow, or slow flow conditions, e.g., using the flow rate of fluid, and/or nominal, over, or under fill conditions, e.g., using the volume of fluid. Alternatively or additionally, sensor 136 may be used to determine changes in pressure within pump 102 and/or infusion assembly 100 or to provide feedback to an active flow control system.

Moreover, although FIGS. 5 and 6 show that infusion assembly 100 may be configured for receipt of a battery, sensor 136 does not require constant power to accurately measure changes in its elongation. In particular, dielectric elastomer sensors provide consistent readings as to their elongation if a measurement or reading device is connected to the sensor or a controller for the sensor to obtain a measurement or reading, then is disconnected, and then is reconnected to obtain another measurement or reading. Even though the measurement or reading device in such a scenario is not continuously connected to the sensor or other component to obtain measurements or readings sensed by the sensor, each time the measurement device is connected, it will obtain a measurement at that moment in time. The various measurements or readings can then be correlated to determine, e.g., a flow rate of fluid from bladder 118, a change in volume of bladder 118, or the like. Accordingly, sensor 136 need not be continuously powered to provide consistent measurements or readings indicating its change in elongation. As such, infusion assembly 100, and particularly pump 102, may be a non-electric assembly even when utilizing sensor(s) 136.

In filling with fluid, bladder 118 expands such that the second circumference in its inflated position is up to approximately three times the first circumference in its deflated position, i.e., the second circumference is larger than the first circumference by as much as a factor of 3. Conversely, as bladder 118 dispels or dispenses fluid held in chamber 134, the circumference of bladder 118 is reduced by up to about 300%, i.e., the first circumference of bladder 118 may be about one-third the size or length of second circumference of bladder 118. As such, bladder 118 has a change in elongation of up to about 300% between its deflated and inflated positions. Therefore, sensor 136 is configured to expand or contract as required to accurately sense or measure a change in elongation of bladder 118 of up to about 300%.

As will be readily understood, the one or more sensors 136 generate each generate one or more outputs providing various information about pump 102 and/or infusion assembly 100, such as the flow rate of fluid from chamber 134 of pump 102 and/or the volume of fluid within chamber 134. Such information may be communicated to a user of infusion assembly 100, e.g., using one or more indicators or signals. As one example, referring to FIGS. 5 and 6, one or more light emitting diodes (LEDs) 140 may be positioned on upper support member 104 to provide a signal indicating a flow condition or volumetric condition of pump 102. For example, a red LED 140 and a green LED 140 may be included on upper support member 104. When illuminated, the red LED 140 signals a no flow condition and when the green LED 140 is illuminated, the green LED 140 signals fluid is flowing at a desired flow rate. As another example, an illuminated red LED 140 may signal chamber 134 contains an incorrect volume of fluid, i.e., that chamber 134 is either underfilled or overfilled, and an illuminated green LED 140 may signal chamber 134 contains a desired volume of fluid.

Other indicators and/or signals also may be used. For example, upper support member 104 may include a control housing 142, which may house a printed circuit board (PCB) and/or other control elements, as well as features such as a wireless relay or module (e.g., a Bluetooth module). In one embodiment, infusion assembly 100 may incorporate a display 144, e.g., positioned at, attached to, or incorporated into upper support member 104 as depicted in FIGS. 7, 8, and 9. Display 144 may provide a visual indication of one or more conditions of pump 102 and/or infusion assembly 100. For example, as shown in FIGS. 8 and 9, display 144 may provide a graphical representation of the change in volume of fluid within chamber 134, e.g., as fluid is dispelled or dispensed from chamber 134 of pump 102. Alternatively or additionally, display 144 may provide a graphical representation of the flow rate of fluid from chamber 134, e.g., indicating whether the flow rate has increased, decreased, or remained constant. In other embodiments, display 144 may provide a numerical indication of the flow rate of fluid from pump 102, the flow rate of fluid to patient P, the volume of fluid remaining in chamber 134, the volume of fluid that has been dispensed to patient P, and/or other numerical information. In still other embodiments, display 144 may indicate the fluid is flowing from pump 102 and/or is flowing to patient P at a target or desired flow rate. Display 144 may indicate other conditions or provide other information as well.

As stated, rather than providing display 144 as a part of infusion assembly 100, display 144 may be part of a separate device that receives information about the flow rate, change in volume of fluid, and the like from infusion assembly 100 to provide via display 144. For example, as shown schematically in FIG. 10, data or information from infusion assembly 100 may be sent to one or more patient or user wireless devices 146, e.g., over or through a communications network or via a wireless relay or module as previously described. Wireless user devices 146 may comprise a personal computing device, such as portable or mobile telecommunications devices, e.g., with Internet functionality. As examples, wireless devices 146 may be desktop computers, tablet computers, smartphones, or any other suitable personal computing devices. In one embodiment, wireless devices 146 are connected to a server 148 through a network 150 to provide and/or receive information at least from infusion assembly 100; other assemblies or medical instruments also may provide data or information to and/or receive data or information from a wireless device 146. It should be appreciated that network communications can comprise sending and/or receiving information over one or more networks 150 of various forms. For example, a network can comprise a dial-in network, a local area network ("LAN"), a wide area network ("WAN"), a public switched telephone network ("PSTN"), the Internet, an intranet, or other type(s) of networks. A network may comprise any number and/or combination of hard-wired, wireless, or other communication links. Further, multiple medical devices or instruments such as infusion assembly 100 may be connected to server 148 via network 150 to provide and/or receive data or information. Preferably, wireless devices 146 are configured to execute one or more computer programs, such as an Internet browser program, to allow users to interact with server 148, and devices 146 preferably include a display 144, such as a monitor or screen, for providing information or data such as the flow rate of fluid from chamber 134, a change in volume of fluid, and the like to patient P, a physician, and/or a caregiver.

In some embodiments, wireless device 146 may utilize a mobile application, i.e., an app, designed to capture inputs from one or more users and to provide outputs to the one or more users. For example, patient P may download the app onto his or her smartphone before or after a medical procedure requiring the use of infusion assembly 100 as part of the recovery process. In some embodiments of the app, a portion of the app may be a log where patient P can provide inputs, e.g., the patient may rate his or her pain or relative pain level once a day or throughout the day, rate the patient's perceived or subjective recovery level, indicate the patient's activity level, or the like. Another portion of the app may be configured similar to a questionnaire, presenting the patient with questions or prompts and allowing the patient to select a pre-generated answer or input an answer. That is, the app may present the patient with answers to choose from, may allow free-form answers, or a combination of both. Further, the app may be tailored to the patient's specific procedure or infusion assembly 100 the patient is using. Other portions of the app may be configured to receive data or information outputs from assembly 100 and to provide such data or information to the user, e.g., via a display 144 incorporated into device 146. In other embodiments, a web-based data collection and presentation tool rather than a mobile app may be used to gather patient-generated data and data generated by infusion assembly 100. The web-based data collection and presentation tool may be configured similarly to the above-described app, e.g., with a log portion, a questionnaire portion, and the like. In other embodiments, rather than operating or communicating wirelessly, a wired user device 152 may be connected to infusion assembly 100 to provide and/or receive data or information to and/or from assembly 100. For example, as depicted in FIG. 11, wired device 152 may connect to assembly 100 at control housing 142 using, e.g., a wire 154 from device 152 that selectively plugs in or connects to housing 142 via a plug or connector 156. Preferably, wired device 152 includes a display 144 for providing information or data such as the flow rate of fluid from chamber 134, a change in volume of fluid, and the like to patient P, a physician, and/or a caregiver. Similar to wireless device 146, in some embodiments wired device 152 may utilize an app or a web-based data collection and presentation tool to gather data from, e.g., patient P and infusion assembly 100 and display information or data to patient P, a physician, or a caregiver.

Thus, in various embodiments, data or information from sensor or sensors 136 may be provided to patient P or other users via a display 144 incorporated into infusion assembly 100, incorporated into a wireless mobile user device, or incorporated into a wired device that may be selectively plugged into assembly 100. Of course, any other suitable configuration of a device having a display 144 may be used as well.

As described above, infusion assembly 100 may generate a number of outputs. For example, infusion assembly 100 may output the flow rate of fluid from expandable bladder 118. Additionally or alternatively, one output from assembly 100 may be a volume of fluid dispensed from bladder 118 over a period of time and/or an output may be a change in the volume of fluid within chamber 134 of bladder 118 over a period of time. More specifically, the one or more outputs may be generated by sensor(s) 136 and/or one or more controls or control assemblies of infusion assembly 100. The one or more outputs may be communicated to a user of assembly 100—such as patient P, a physician, and/or a caregiver—using one or more visual, tactile, audible, or other indicators. In particular, an output may provide information to a user via an indicator such as one or more LED lights 140 and/or a display 144. Other forms of data or information, and other configurations of indicators for communicating such data or information, may be used as well.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An elastomeric pump for an infusion assembly, the pump comprising:
    an upper support member;
    a lower support member spaced apart from the upper support member along an axial direction;
    an expandable bladder defining a chamber, the bladder extending from the upper support member to the lower support member; and
    a first flexible dielectric elastomer sensor coupled on a first end to the upper support member and on a second, opposite end to the lower support member, the first flexible dielectric elastomer sensor extending from the upper support member to the lower support member along a portion of a circumference of the expandable bladder,
    the first flexible dielectric elastomer sensor is configured to contact only a portion of the expandable bladder to measure a change in elongation of the expandable bladder,
    the first flexible dielectric elastomer sensor is positioned externally to the expandable bladder such that the first flexible dielectric elastomer sensor is in contact with an exterior surface of the expandable bladder,
    the first dielectric elastomer sensor can measure a change in elongation of the expandable bladder, and
    the expandable bladder expands radially to an inflated position having a generally spherical shape.

2. The pump of claim 1, further comprising at least two additional flexible dielectric elastomer sensors, wherein the at least two additional flexible dielectric elastomer sensors extend between the upper support member and the lower support member.

3. The pump of claim 2, wherein the first sensor flexible dielectric elastomer and the at least two additional flexible dielectric elastomer sensors are evenly spaced such that a same circumferential length separates each sensor at an axial position along the expandable bladder.

4. The pump of claim 1, further comprising at least one indicator for providing information about the pump, wherein the information is based on the change in elongation of the expandable bladder.

5. An infusion assembly comprising:
    an elastomeric pump having an upper support member, a lower support member, and an expandable bladder extending between the upper support member and the lower support member, the expandable bladder having an outer surface and defining a chamber;
    a first flexible sensor in contact with the outer surface of the expandable bladder and coupled on a first end to the upper support member and on a second, opposite end to the lower support member, the first flexible sensor extending along an entire length of the expandable bladder, wherein the first flexible sensor is a dielectric elastomer sensor; and
    at least one indicator for indicating one or more outputs of the first flexible sensor, where:
        the at least one indicator comprises a first light emitting diode (LED) indicator and a second LED indicator,
        the first LED indicator is a different color from the second LED indicator,
        a majority of the outer surface of the expandable bladder is visible such that a user can visually discern a change in elongation of the bladder, and the expandable bladder expands radially to an inflated position having a generally spherical shape.

6. The infusion assembly of claim 5, wherein the at least one indicator comprises a display.

7. The infusion assembly of claim 5, wherein the display is positioned at the upper support member.

8. The infusion assembly of claim 6, wherein the display is incorporated into a wireless user device.

9. The infusion assembly of claim 6, wherein the display is incorporated into a wired user device that is selectively plugged into a control housing of the pump.

10. The infusion assembly of claim 5, wherein one output is a flow rate of fluid from the expandable bladder.

11. The infusion assembly of claim 5, wherein one output is a volume of fluid dispensed from the expandable bladder.

12. The infusion assembly of claim 5, wherein the first LED indicator is separate from the second LED indicator.

13. The infusion assembly of claim 5, wherein the first LED indicator is configured to indicate a no flow condition of the infusion assembly and the second LED indicator is configured to indicate a fluid is flowing through the infusion assembly at a desired flow rate.

14. The infusion assembly of claim 13, wherein the first LED indicator is a red LED and the second LED indicator is a green LED.

15. The pump of claim 1, wherein the upper support member is provided at a proximal end of the expandable bladder and the lower support member is provided at an opposing distal end of the expandable bladder.

16. The pump of claim 1, further comprising a second flexible dielectric elastomer sensor extending circumferentially about a center portion of the expandable bladder, wherein the first flexible dielectric elastomer sensor partially overlaps the second flexible dielectric elastomer sensor.

17. The pump of claim 1, wherein the expandable bladder expands up to 300% between a deflated position and the inflated position.

* * * * *